United States Patent [19]

Geeham

[11] Patent Number: 5,295,481
[45] Date of Patent: Mar. 22, 1994

[54] CARDIOPULMONARY RESUSCITATION ASSIST DEVICE

[76] Inventor: Calvin T. Geeham, 12761 138th La. N., Largo, Fla. 34644

[21] Appl. No.: 786,380

[22] Filed: Nov. 1, 1991

[51] Int. Cl.$^5$ .................... A61H 31/02; A61N 1/00
[52] U.S. Cl. .................................................... 601/43
[58] Field of Search ............... 128/419 D, 52, 53, 54, 128/28, 802, 419 G, 419 S, 30.2, 30; 600/16; 4/255, 256; D24/164, 167

[56] References Cited

U.S. PATENT DOCUMENTS

| | | | |
|---|---|---|---|
| 219,428 | 9/1879 | Armstead | 4/255 |
| 3,747,605 | 7/1973 | Cook | 128/419 D |
| 3,955,563 | 5/1976 | Maione | 128/53 |
| 4,196,722 | 4/1980 | VanderWoude | 128/28 |
| 4,273,114 | 6/1981 | Barkalow et al. | 128/53 |
| 4,928,674 | 5/1990 | Halperin et al. | 128/30.2 |

OTHER PUBLICATIONS

News Broadcast of WDIV ∝ TV in Detroit Featuring Segment on CPR Conducted with Plunger, Jun. 1992.
Detroit Free Press Article "Toilet Plunger Inspires Hand-Held CPR Device", dated Nov. 12, 1991, p. 11A.
"Active Compression-Decompression, A New Method of Cardiopulmonary Resuscitation" JAMA 267, 21 pp. 2916-2923, Jun. 3, 1992.
"CPR: The P Stands for Plumber's Helper", JAMA 264, 13, p. 1661 Oct. 3, 1990.

Primary Examiner—Richard J. Apley
Assistant Examiner—John P. Leubecker
Attorney, Agent, or Firm—Peter D. Keefe

[57] ABSTRACT

A device providing performance of CPR without need to exert forces of such magnitude that the patient may be injured, and which further provides performance of defibrillation and ventilation. The CPR assist device according to the present invention is composed generally of an elongate column member, handles mounted normal to the column member, a suction cup member mounted at one end of the column member, and a defibrillation system so that the patient may be defibrillated in conjunction with CPR. According to the method of the present invention, an aid giver places the suction cup member of the CPR assist device on the chest of the patient, then grabs the handles and proceeds to alternately press on the chest and pull from the chest. The suction cup member causes the chest to compress and expand, thereby creating a churning action within the chest cavity that resuscitates the patient. An added benefit of the CPR assist device is that the expansion of the chest cavity as the suction cup member is pulled away from the chest will stimulate lung action of the patient. Defibrillation is provided by the aid giver actuating one or more switches on the column member which supplies electrical stimulation at electrodes mounted to the suction cup member. The defibrillation circuit may operate from household current or may be powered by an internal battery.

10 Claims, 2 Drawing Sheets

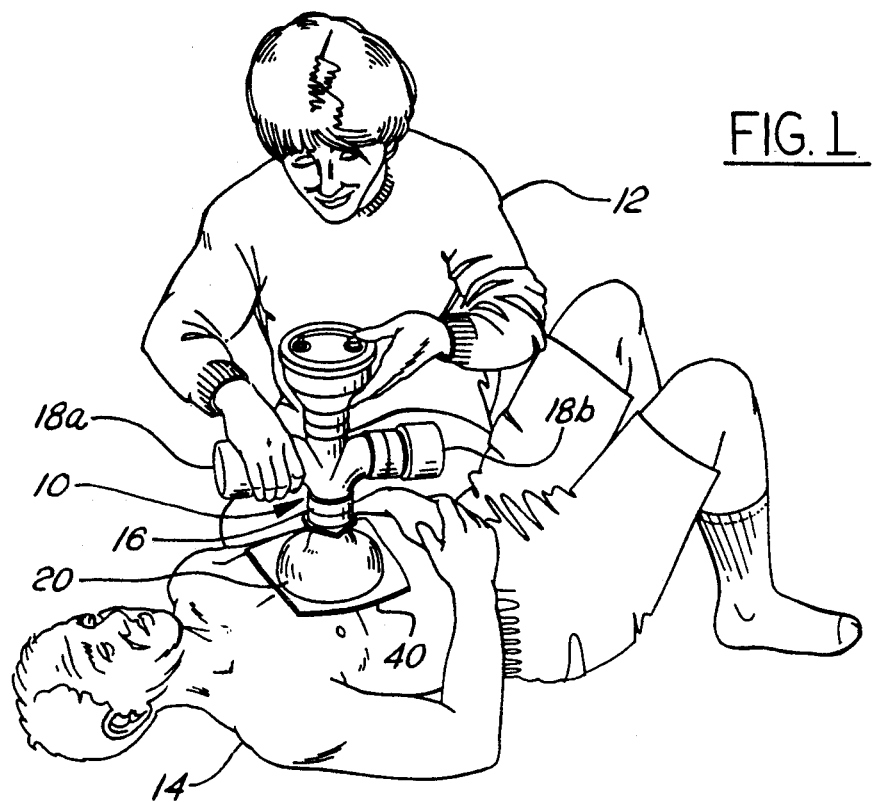
FIG. 1
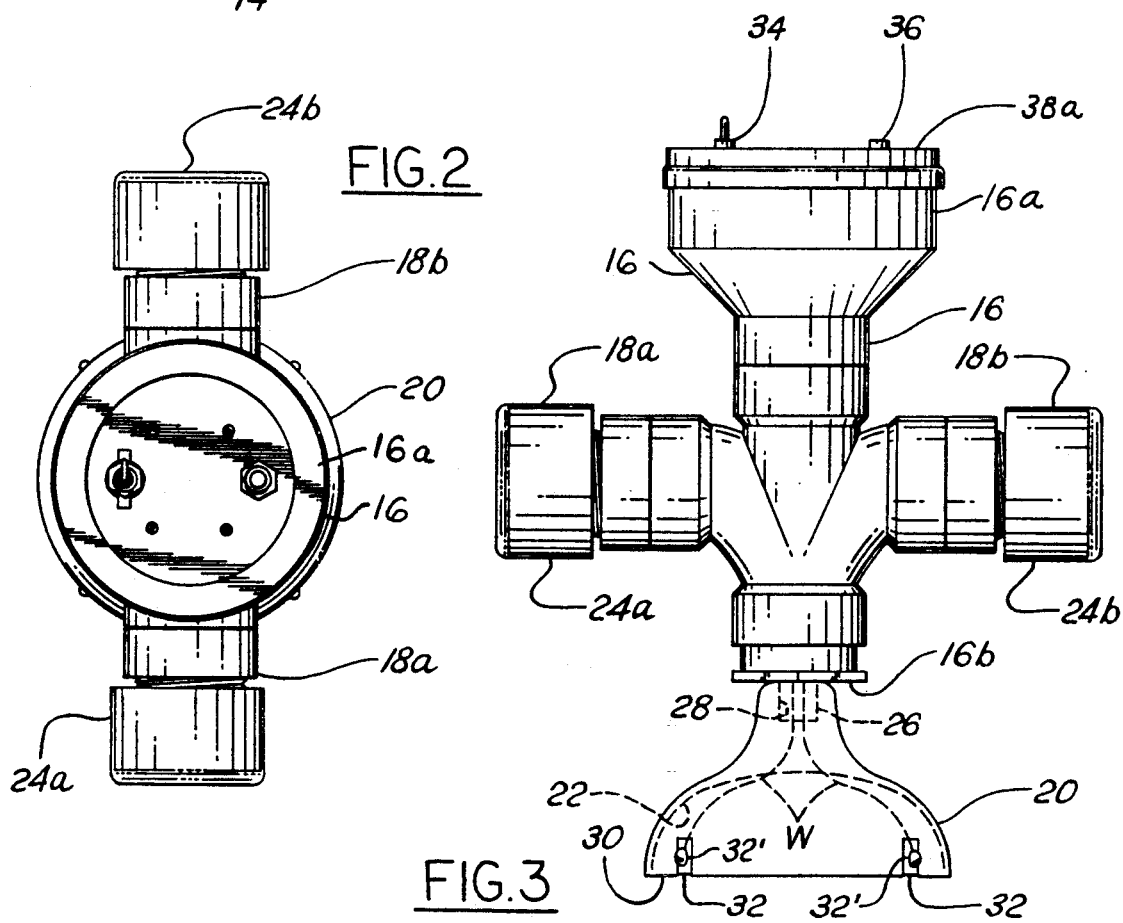
FIG. 2
FIG. 3

CARDIOPULMONARY RESUSCITATION ASSIST DEVICE

BACKGROUND OF THE INVENTION

1. Field of the Invention

The present invention relates to the process of cardiopulmonary resuscitation (CPR), and more particularly to a device which aids in the performance of CPR.

2. Description of the Prior Art

Cardiopulmonary resuscitation, hereinafter ref erred to as "CPR", has become a standard first aid technique to attempt revival of at person who has suffered cardiac arrest. In CPR, the heels of both hands are placed one over the other, so as to periodically apply a force to the chest between the middle and lower third of the sternum. The force is applied about 60 to 80 times per minute. Ordinarily, the force required is considerable, on the order of 80 pounds, so that the chest may be pushed vertically downward 1.5 to 2 inches. A problem that can arise from this amount of force can include broken ribs, a lacerated liver, or other internal organ damage that itself can be lethal to the patient.

In the event cardiac arrest continues or cardiac rhythm is life-threatening defibrillation has become a standard technique of correction. In defibrillation, an electrical stimulation is provided to the chest which shocks the heart muscle, and thereby causes the heart to begin beating in its normal manner.

Another serious problem associated with cardiac arrest is that the patient may cease breathing. In the art it is the established practice to establish an airway in the patient, then administer mouth-to-mouth ventilation. A problem arises when ventilation must accompany CPR.

What is needed in the art is a way in which to perform CPR without need to exert forces of such magnitude that the patient may be injured, and further in which to perform defibrillation, as well as to perform ventilation.

SUMMARY OF THE INVENTION

The present invention is a device which permits performance of CPR without need to exert forces of such magnitude that the patient may be injured, and which further provide performance of defibrillation and ventilation.

The CPR assist device according to the present invention is composed generally of an elongate column member, handles mounted normal to the column member, and a suction cup member mounted at one end of the column member. The CPR assist device is further preferred to be equipped with a defibrillation system so that the patient may be defibrillated in conjunction with CPR.

In operation, an aid giver places the suction cup member of the CPR assist device on the chest of the patient, then grabs the handles and proceeds to alternately press on the chest and pull from the chest. The suction cup member causes the chest to compress and expand, thereby creating a churning action within the chest cavity that resuscitates the patient. An added benefit of the CPR assist device is that the expansion of the chest cavity as the suction cup member is pulled away f rom the chest will stimulate lung action of the patient.

The CPR assist device according to the present invention also provides defibrillation by the aid giver actuating one or more switches on the column member which supplies electrical stimulation at electrodes mounted to the suction cup member. The defibrillation circuit may operate from household current or may be powered by an internal battery.

Accordingly, it is an object of the present invention to provide a CPR assist device which allows an aid giver to render CPR to a patient without need to apply extreme force to the patient's chest.

It is another object of the present invention to provide a CPR assist device which allows an aid giver to provide both positive and negative forces on the patient's chest cavity, thereby providing a churning action within the patient's body which provides blood circulation.

It is a further object of the present invention to provide a CPR assist device in which defibrillation may be administered to the patient in conjunction with CPR.

It is a yet another object of the present invention to provide a CPR assist device, in which defibrillation may be administered to the patient in conjunction with CPR, further in which defibrillation voltage is selectable between a high and a low voltage.

It is still a further object of the present invention to provide a CPR assist device which allows an aid giver to provide both positive and negative forces on the patient's chest cavity, thereby providing a churning action within the patient's body which provides blood circulation and ventilation.

These, and additional objects, advantages, features and benefits of the present invention will become apparent from the following specification.

BRIEF DESCRIPTION OF THE DRAWINGS

FIG. 1 is a perspective view of the CPR assist device according to the present invention, shown in operation in connection with a patient and an aid giver.

FIG. 2 is a top plan view of the CPR assist device according to the present invention.

FIG. 3 is a side view of the CPR assist device according to the present invention.

DETAILED DESCRIPTION OF THE PREFERRED EMBODIMENT

Figure 4:
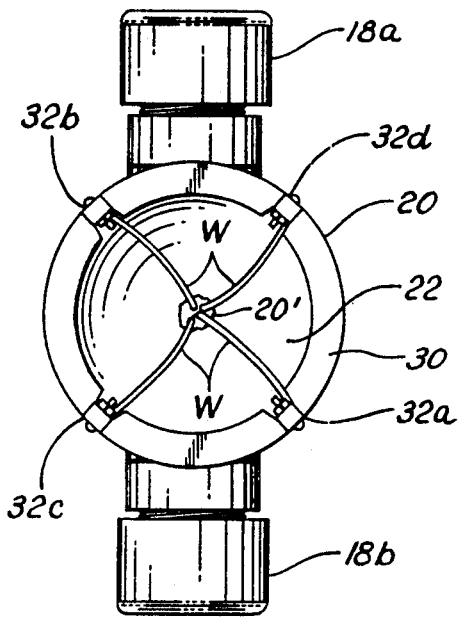
FIG. 4 is a bottom view of the CPR assist device according to the present invention.

Referring now to the Drawing, FIG. 1 shows the CPR assist device 10 according to the present invention being used by an aid giver 12 in order to attempt resuscitation of a cardiac patient 14. The CPR assist device is composed generally of a column member 16 to which is attached at right angles thereto a pair of handles 18a and 18b, and a suction cup member 20 which is attached at one end of the column member 16 in an orientation which points the concave internal surface 22 of the suction cup member 20 away from the column member 16.

It is preferred to construct the column member and handles from a plastic material. It is further preferred for one or both of the handles 18a, 18b to be equipped with threaded end caps 24a, 24b which, as shown in the Drawing, form a functional part of the handles. The end caps 24a, 24b may be unthreaded to reveal a storage cavity for holding various first aid devices, such as a mouth-to-mouth ventilator tube, a tourniquet, smelling salts, etc.

The handles 18a, 18b are preferred to be located about in the middle of the column member 16, between an upper end 16a and a lower end 16b. The handles 18a, 18b are of sufficient length that an aid giver can conveniently place his or her hands thereupon.

At the lower end 16b of the column member 16 is attached the suction cup member 20 in a manner well known in the art, such as a stud 26 connected with the column member fitting into a blind bore 28 of the suction cup member, as shown in FIG. 3. The suction cup member 20 is composed of a resilient rubber or rubber-like material, such as is used for common suction cup applications. The suction cup member 20 includes an internal concave surface 22 defined by a peripheral rim 30. A preferred cross-reaction for the peripheral rim 30 is on the order of six inches, although this is not a requirement.

It is preferred for the CPR assist device to include a defribillation system. Defibrillation is provided by electrical contact between the patient's chest and two or more electrodes 32 located at the peripheral rim 30, and connected thereto by any practical means known in the art. As an example shown in FIGS. 3 and 4, the electrodes 32 may be U-shaped so as to fold around the peripheral rim 30 and then bolt to the suction cup member 20 via bolts 32'. In the examples shown in the Drawing, two pairs of electrodes 32a, 32b, and 32c, 33d are provided. The first set of electrodes 32a, 32b are connected to a low voltage circuit $C_1$, have opposite polarity and are located at opposite positions on the peripheral rim 30. The second set of electrodes 32c, 3d are connected to a high voltage circuit $C_2$, have opposite polarity and are located at opposite positions on the peripheral rim 30. Other electrode configurations are possible, and it is preferred for each set of electrodes to be well separated from any other set of electrodes. The upper end 16a of the column member 16 is provided with switches 34 and 36 which respectively control the low and high voltage circuits. These switches may be momentary (preferred for the high voltage circuit), or non-momentary (preferred for the low voltage circuit) on-off type switches, and they may be further associated with CPR assist device circuitry which provides periodic pretimed shocks of electricity to the electrodes, predetermined or user controlled levels of current, voltage and power to the electrodes. A transformer T provides a boost or reduction in the voltage, a transformer being optionally in either or broth, the high and low voltage circuits.

Figure 5:
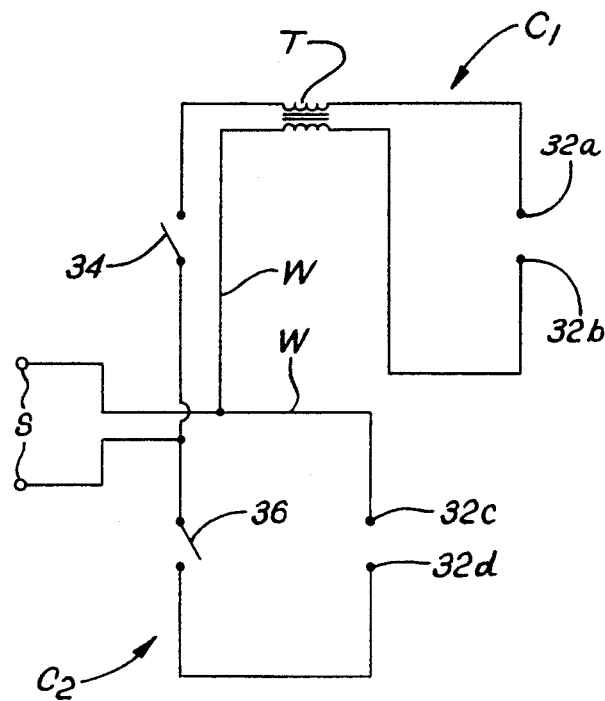
FIG. 5 is an electrical schematic for a first variation of the CPR assist device according to the present invention which uses household electricity.

FIG. 5 is a schematic of an electrical circuit in which law voltage is supplied to the first set of electrodes 32a, 32b and further in which high voltage is supplied to the second Bet of electrodes 32c, 32d. In the example shown in FIG. 5 an input electrical source S is provided, which may be provided by a utility, such as household current.

Figure 6:
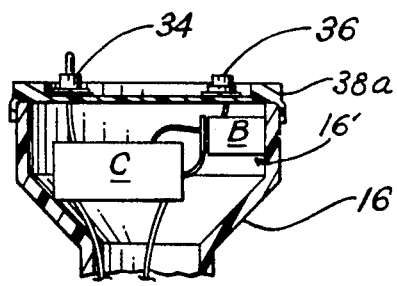
FIG. 6 is a partly sectional, fragmentary side view of a second variation of the CPR assist device according to the present invention, showing in particular selected electrical components.
Figure 7:
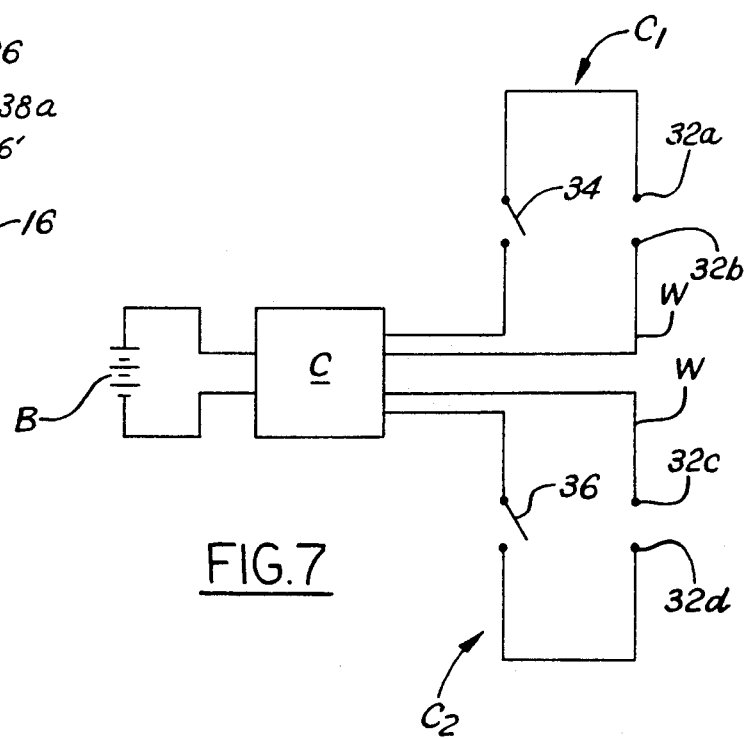
FIG. 7 is an electrical schematic for a second variation of the CPR assist device according to the present invention which uses an internal battery to supply electricity.

It is also possible to construct the CPR assist device so that it contains an internal power supply. FIG. 6 shows a portion of the column member 16 adjacent the upper end 16a, whereat is internally located a battery B for supplying electricity to the defibrillation system. A threaded cap 38a threadingly engages the upper end 16a of the column member 16 so that access to the battery compartment 16' can be achieved for purposes of battery maintenance. The battery may be of the chargeable or nonchargeable types. A converter C is included in the circuit shown in FIG. 7, so that the voltage of the battery, can be boosted to the levels required for the circuits $C_1$ and $C_2$ described above. Circuits $C_1$ and $C_2$ deliver levels of electrical current, voltage and power to the patient via the electrodes 32 which are known in the art of defibrillation to be both medically safe and effective. The battery B is of sufficient ampere-hour rating to supply this electrical requirement. The wires W of circuits $C_1$ and $C_2$ emanate from the apex of the suction cup member and sealed by a resilient seal material 20'.

In operation, after the aid giver has established an airway for the patient in the manner well known in the art, the aid giver grabs hold of the handles of the CPR assist device and placed the suction cup member so that it is upon the chest of the patient. The aid giver then administers cycles of compression and expansion of the chest of the patient by pressing down on the chest and pulling up away from the chest. The structure of the column member and the resiliency of the suction cup member provide a transfer of force safely and noninjuriously to the chest of the patient. The act of pulling the CPR assist device away from the patient's chest results in a suction action within the suction cup member that draws the chest upwardly with the movement of the suction cup member. Thusly, the chest cavity is forced to undergo a deep churning action, without need of the high forces required in conventional CPR, which enhances and stimulates blood flow, while simultaneously ventilating the patient.

If CPR alone is not sufficient to revive the patient, the aid giver then administers defibrillation by placing an electrode pad 40 under the peripheral rim and then actuating selected switches. The electrode pad 40 is made of a material well known in the art of defibrillation which serves to protect the patient from burns at the electrodes 32. Generally, the lower voltage would be first attempted, followed by the high voltage if the former were unsuccessful at reviving the patient. Defibrillation can thereafter continue during further CPR procedures as described hereinabove.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A cardiopulmonary resuscitation assist device for providing cardiopulmonary resuscitation to the chest of a cardiac patient by an aid giver, comprising:
   a column member having an upper end and a lower end;
   a suction cup member connected with said lower end of said column member, said suction cup member having an internal substantially concave surface facing away from said column member, said internal substantially concave surface being defined by a peripheral rim, said suction cup member being constructed of a resilient material;

defibrillation means connected with said column member for supplying defibrillating electrical shock to the chest of the cardiac patient; and handle means connected to said column member between said upper end and said lower end thereof for providing a handhold substantially perpendicular with respect to said column member;

wherein the aid giver places said peripheral rim of said suction cup member upon the chest of the cardiac patient, then subsequently applies forces at said handle means alternately toward and away from the chest of the cardiac patient so as to provide cardiopulmonary resuscitation, the application of force away from the chest of the cardiac patient causing the chest of the cardiac patient to move with the suction cup member due to a suction effect between the suction cup member and the chest of the cardiac patient.

2. The cardiopulmonary resuscitation, assist device of claim 1, wherein said means defibrillation comprises:

a plurality of electrodes connected to said peripheral rim of said suction cup member; and electrical circuit means for selectively supplying electricity to said plurality of electrodes so as to provide defibrillation for the cardiac patient.

3. The cardiopulmonary resuscitation assist device of claim 2, wherein said circuit means comprises at least two circuits, each circuit of said at least two circuits uniquely provides a respective preselected voltage at said plurality of electrodes.

4. The cardiopulmonary resuscitation assist device of claim 3, wherein each said circuit on with pair of 5. The cardiopulmonary resuscitation assist device of claim 2, wherein said handle means comprises a pair of handles, at least one handle of said pair of handles having an interior cavity for storing medical supplies; further comprising an end cap threadably connected with at least one handle of said pair of handles for providing access to said interior cavity.

6. The cardiopulmonary resuscitation assist device of claim 2, wherein said electrical circuit means further comprises battery means for supplying electricity to said electrode.

7. The cardiopulmonary resuscitation assist device of claim 6, wherein said circuit means comprises at least two circuits, each circuit of said at least two circuits uniquely provides a respective preselected voltage at said plurality of electrodes.

8. The cardiopulmonary resuscitation assist device of claim 7, wherein each said circuit is connected with a respective pair of electrodes of said plurality of electrodes.

9. The cardiopulmonary resuscitation assist device of claim 2, wherein said electrical circuit means further comprises circuitry means for providing user controlled levels of current, voltage and power to said electrodes.

10. A method for providing cardiopulmonary resuscitation (CPR) to the chest of a cardiac patient by an aid giver, for use with a CPR assist device comprising a column member, a suction cup member connected to said column member, and a defibrillation means connected to said column member for supplying defibrillating electrical shock, comprising the steps of:

placing said suction cup member upon the chest of the cardiac patient;

applying forces on said suction cup member alternately toward and away from the chest of the cardiac patient with a predetermined timing therebetween so as to provide cardiopulmonary resuscitation, the application of force away from the chest of the cardiac patient causing the chest of the cardiac patient to move with the suction cup member due to a suction effect between the suction cup member and the chest of the cardiac patient; and activating said defibrillating means to selectively apply a defibrillating shock to the chest of the cardiac patient while said suction cup member is adjacent to the chest during said period of predetermined timing between application of forces.

* * * * *